US006790304B2

(12) United States Patent
Fox et al.

(10) Patent No.: US 6,790,304 B2
(45) Date of Patent: Sep. 14, 2004

(54) METHOD OF MANUFACTURING A LEAP-TYPE TESTING IMPLEMENT

(76) Inventors: Robert Fox, 42 Tritown Cir., Mashpee, MA (US) 02649; Thomas J. Hardiman, 9 Central Ave., Plymouth, MA (US) 02360

( * ) Notice: Subject to any disclaimer, the term of this patent is extended or adjusted under 35 U.S.C. 154(b) by 224 days.

(21) Appl. No.: 10/053,102

(22) Filed: Nov. 13, 2001

(65) Prior Publication Data

US 2003/0089448 A1 May 15, 2003

(51) Int. Cl.[7] .................. B32B 31/10; B32B 31/12; A61B 19/00
(52) U.S. Cl. ............... 156/201; 156/204; 156/252; 156/257; 156/464; 156/519; 600/557
(58) Field of Search .................. 156/201, 204, 156/252, 257, 260, 271, 276, 297, 464, 519, 520, 552, 202; 53/134.2; 493/221; 600/557, 587

(56) References Cited

U.S. PATENT DOCUMENTS

| | | | |
|---|---|---|---|
| 2,469,536 A | * | 5/1949 | Winesett ............... 493/221 |
| 2,597,884 A | * | 5/1952 | Marks |
| 3,191,355 A | * | 6/1965 | Morpurgo |
| 3,202,064 A | * | 8/1965 | Kennedy |
| 3,316,686 A | * | 5/1967 | Welin-Berger |
| 3,511,735 A | * | 5/1970 | Lindley |
| 3,616,083 A | * | 10/1971 | Mohr |
| 4,021,289 A | * | 5/1977 | Orzelek et al. |
| 4,091,680 A | | 5/1978 | Block |
| 4,218,278 A | * | 8/1980 | McMackin et al. |
| 4,750,966 A | * | 6/1988 | Koller |
| 4,807,938 A | * | 2/1989 | Weihrauch |
| 6,090,050 A | | 7/2000 | Constantinides |
| 6,113,551 A | | 9/2000 | Isaacs et al. |
| 6,196,976 B1 | | 3/2001 | Christy |
| 6,200,272 B1 | * | 3/2001 | Linden |
| 6,207,000 B1 | * | 3/2001 | Schwobel et al. |
| 2002/0092612 A1 | * | 7/2002 | Davies et al. |

FOREIGN PATENT DOCUMENTS

| | | |
|---|---|---|
| DE | 43 37 608 | 6/1995 |
| WO | WO 99/41565 | 8/1999 |

OTHER PUBLICATIONS

Landrock, *Adhesives Technology Handbook*, pp. 205–218, 1985.*

"Foot Screening–Care of the Foot in Diabetes," Dept. of Health & Human Services, USA, U.S. Government Print Office (1998).

Birke et al., "Evaluation of a Self–Administered Sensory Testing Tool to Identify Patients at Risk of Diabetes–Related Foot problems," *Diabetes Care*, vol. 21, No. 1 (Jan. 1998).

McGill M. et al.: "Use of Semmes–Weinstein 5.07/10 Gram Monofilament: the Long and the Short of it" Diabetic Medicine: A Journal of the British Diabetic Association. England Jul. 1998, vol. 15, No. 7, Jul. 1998, pp. 615–617 XP009008005 ISSN: 0742–3071.

* cited by examiner

*Primary Examiner*—Steven D. Maki
(74) *Attorney, Agent, or Firm*—Nutter McClennen & Fish LLP

(57) ABSTRACT

An automated process of making a medical test implement, such as a LEAP Testing Implement, includes the steps of providing a handle element, providing a deformable test element, and mechanically mating the deformable test element to the handle element so that at least a portion of the deformable test element extends from the handle element. The deformable test element deforms when a predetermined load is applied thereto.

20 Claims, 5 Drawing Sheets

METHOD OF MANUFACTURING A LEAP-TYPE TESTING IMPLEMENT

BACKGROUND OF THE INVENTION

The present invention relates to medical technology, and more particularly to a method of manufacturing an implement for identifying patients at risk of developing diabetes-related foot problems.

Approximately 16,000,000 Americans are currently afflicted with diabetes, with another 800,000 new cases of the disease, on average, diagnosed among the American population each year. Both of these figures are expected to increase in the future, however, as there has been a 37% rise in the number of Americans diagnosed with diabetes in the last ten years.

Diabetes is a very serious disease, complications from which may lead to disabling conditions such as blindness, nerve damage and/or amputation, or to potentially fatal problems such as heart disease, stroke and/or kidney failure. Currently, diabetes is the seventh leading cause of death among Americans.

Among the factors that contribute to disabilities and/or fatalities within the diabetic population is the inability to either predict the occurrence, or to detect the onset of the complications which cause them. In many cases, symptoms of the onset of diabetic complications are undetectable. Furthermore, even in the instances where tests are available to accurately detect the onset of such complications, the tests are often painful, time-consuming and/or cost prohibitive to perform.

One notable exception, however, is a current test used to predict potential foot complications associated with diabetes.

Approximately 15–20% of the diabetic population will develop foot (i.e. plantar) ulcers during their lifetime due to diabetic neuropathy. And of the approximately 90,000 lower extremity amputations performed on the diabetic population each year, 85% are performed on those who had previously developed foot ulcerations. Moreover, approximately 50% of these amputees develop foot ulcers on their non-affected foot within eighteen months of amputation. Thus, the benefits of preventing foot ulcers among diabetics are abundantly clear.

The economic considerations of diabetic foot ulcerations are of increasing concern and continue to rise. Studies indicate that the cost of treating a diabetic foot ulcer can range from $1,929 to $6,664 and the cost for a lower extremity amputation can range from $20,248 to beyond $45,000. Fortunately, in 1992, a Lower Extremity Amputation Prevention (LEAP) program was developed by the Gillis W. Long Hansen Disease Center of Carville, La. (a division of the Bureau of Primary Health Care) to detect diabetic neuropathy and, consequently, to reduce the incidence of foot ulcers and resulting amputations among the diabetic population. The LEAP program includes five major components: annual foot screening; patient education; daily self-inspection of the feet; appropriate footwear selection; and management of simple foot problems.

At the foundation of the LEAP program is the foot screening component, which seeks to identify diabetics who have lost protective foot sensation. Between approximately 20% and 50% of individuals that have had diabetes for ten or more years will ultimately develop some form of peripheral sensory neuropathy. This affliction affects the bottoms (i.e., plantar aspect) of the feet, and manifests itself via a loss of sensation that begins in the toes and ultimately progresses back toward the heel.

To screen for loss of foot sensation among diabetics, a clinician tests a minimum of five plantar sites (see A, B, C, D, E in FIG. 1) on each foot of a patient by pressing a testing implement against each site until the testing device buckles, all-the-while monitoring whether the patient can detect the force created by the testing implement against his/her feet. A patient's inability to detect sensation will signal to the tester that the patient is at high risk for plantar ulceration.

The testing process is quick, painless and inexpensive, but if done incorrectly, is entirely useless. For example, if not enough force is used, even a person with no loss of sensation will not be able to detect the pressure created by the testing device. By contrast, if too much force is used, a person with sensory loss will be able to detect the pressure created by the testing device despite his or her loss of sensation.

Tests have shown that such sensory diabetic foot screening/testing is best performed by using a nylon monofilament testing implement to apply ten grams of axial force to each of the five plantar test sites. Usage of such a device capable of producing this amount of force ensures a dependable method of assessment of the critical threshold of diabetic neuropathy and, in particular, whether or not there is a loss of protective sensation in the foot that could forecast the potential onset of plantar ulceration.

Of course, without some type of tool or gauge, accurate and consistent application of ten grams of axial force is practically impossible. Accordingly, a simple test device, known as a LEAP Testing Implement and shown in FIG. 2, was developed. In 1992 the original paper handled monofilament intended for diabetic foot screening was developed by the staff of the Gillis W. Long Hansen's Disease Center located in Carville, La. to be utilized by the Lower Extremity Amputation Prevention Program developed and supported by the Health and Human Service/Bureau of Primary Health Care. This diabetic foot screening/testing device or LEAP testing Implement includes a 5.07/10 gram test element 2 that is attached to a handle element 4 such that the test element will deform when ten grams of force is applied axially to its free end (e.g., when applying force to a plantar site 6 as shown in FIG. 3).

For a LEAP Testing Implement to function properly (i.e., to have the test element deform at the correct force level) the test element 2 should lie at approximately a right angle, $\alpha$, with respect to the handle element 4 as shown in FIG. 2. Moreover, a specific length, L, of the test element that is equal to 38 millimeters plus or minus one millimeter should extend beyond the handle element 4. If this length is too short (i.e., is less than 37 millimeters in length), a greater force level will be required to deform the test element 2, and there arises a risk of false negative test results, while if the test element is too long (i.e., is greater than 39 millimeters in length), a lesser force level will deform it and could cause false positive results.

Because of the small length of the test element portion of LEAP Testing Implement, and the even smaller difference between an acceptable test element length and an unacceptable test element length, a mere visual inspection of a test element by the unaided eye and/or a comparison of the length of one test element to the length of another will not reveal whether a test element 2 portion of a LEAP Testing Implement is the proper length. As such, those who use LEAP Testing Implements as diagnostic tools must be assured that each Testing Implement was manufactured to exact specifications such that the test element portion 2 thereof has a length of between 37 millimeters and 39 millimeters extending from the handle element 4.

Presently, LEAP Testing Implements are manufactured by hand, wherein one or more individuals assembles each Testing Implement by placing a test element 2 at a specific point on an adhesive-coated handle element 4 and then folding a portion of the handle over the adhesive and part of the test element. Such an inexact manufacturing system is replete with opportunities for the production of unacceptable LEAP Testing Implements. Moreover, even if a LEAP Testing Implement assembler is somehow able to detect that he or she has made an unacceptable Testing Implement, it would be difficult, if not impossible, for him or her to reverse the assembly steps because, by the time the mistake is discovered, the adhesive would likely have already dried.

Not surprisingly, the Bureau of Primary Health Care has indicated that the rejection rate for such hand-assembled LEAP Testing Implements is generally in the range of 20% to 30%. Knowing this, manufacturers often employ measures in an effort to detect and remove unacceptable LEAP Testing Implements prior to their shipment to end users. This necessitates the hiring of extra personnel, which, in turn, translates into a price increase for the LEAP Testing Implements. Moreover, most believe that even with the addition of such detection measures, unacceptable Testing Implements are nevertheless being distributed to end users for testing.

Therefore, in view of the public good that can be obtained though the use of LEAP Testing Implements, a need exists for a method of manufacturing such Testing Implements in such a way as to guarantee both their quality and diagnostic accuracy, while not raising their cost of manufacture so much that the resulting device is rendered cost prohibitive to manufacture and/or use.

SUMMARY OF THE INVENTION

The present invention overcomes the disadvantages of hand fabrication of LEAP Testing Implements by providing a mechanical/automated method for their manufacture.

The method generally includes the steps of providing handle-forming and test element materials, scoring the handle-forming material, and then mechanically folding a first portion of the handle-forming material toward a second portion of the handle-forming material. The deformable test element material is then mechanically placed at a selected point between the first and second portions of the handle-forming material, after which the first and second handle-forming material portions are sealed together by machine components with the test element material therebetween. The handle-forming and test element materials are then mechanically cut to form the handle element and the test element of a LEAP Testing Implement.

In an exemplary aspect of the invention, the test element material is provided via a roll or spool and, prior to being sealed between the first and second portions of the handle-forming material, is heated at a predetermined temperature for a predetermined time in order to ensure the removal of any residual curvature thereof.

In an alternate aspect of the invention, the test element material, in lieu of being fed via a roll or spool, is instead fed in pre-cut lengths from a hopper feed mechanism.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
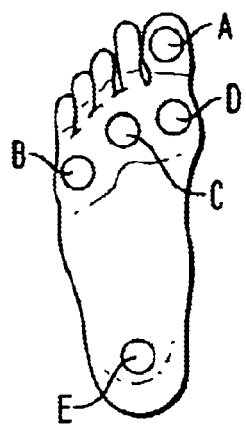
FIG. 1 is an illustration of a right human foot, wherein plantar sites are identified by the letters A, B, C, D and E.

The present invention describes an automated process for producing medical test elements such as the LEAP Testing Implement described above with respect to FIGS. 1–3. Such elements are sometimes referred to in the art either as Aesthesiometers© or Aaesthesiometers©.

Figure 4:
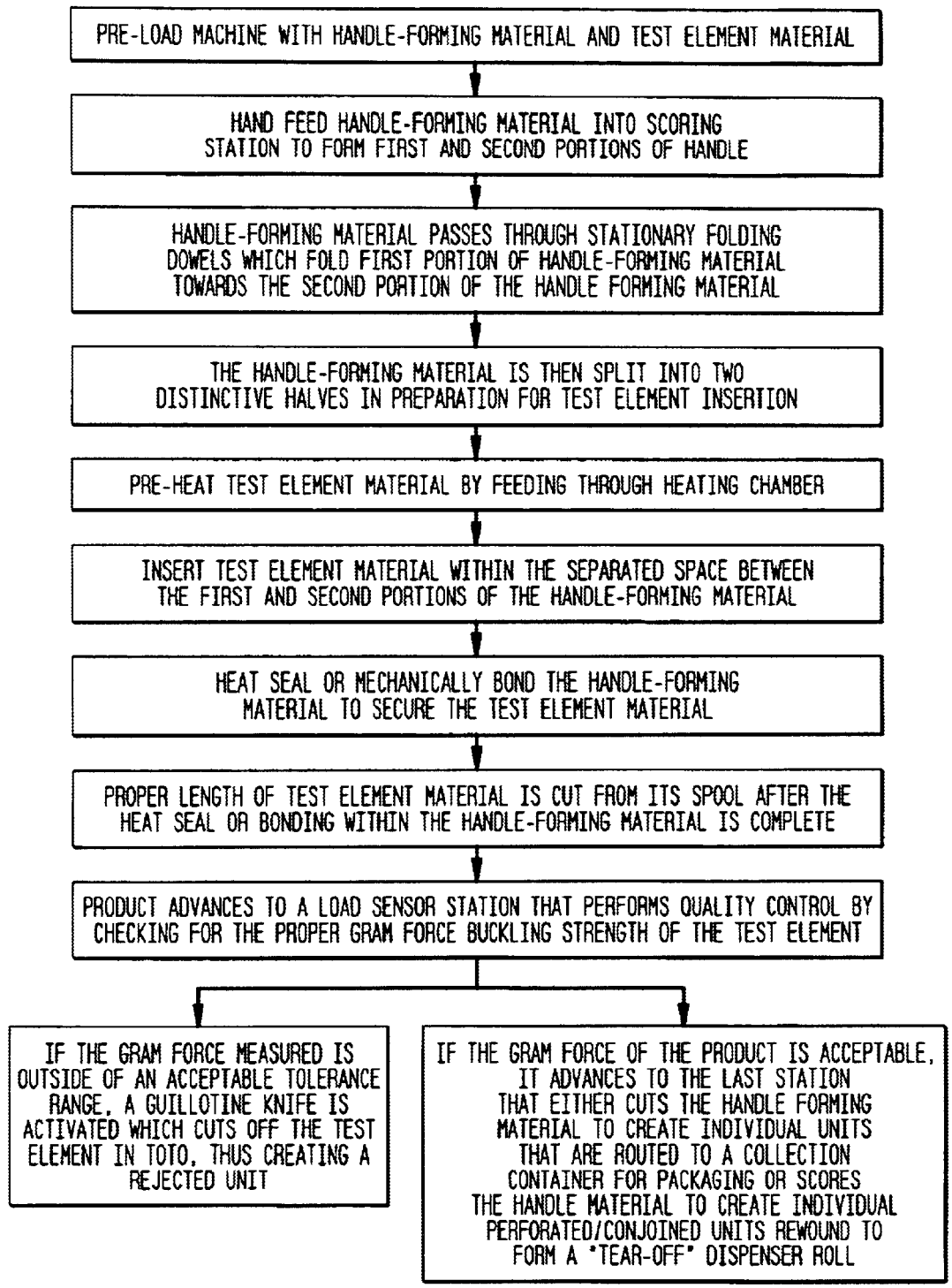
FIG. 4 is a flow diagram illustrating an exemplary process of mechanically manufacturing a LEAP Testing Implement according to the present invention.

As shown in the flow diagram of FIG. 4, this process generally includes the steps of providing handle-forming and test element materials, scoring the handle-forming material, and then folding a first portion of the handle-forming material toward a second portion of the handle-forming material. The process further includes heating the deformable test element material and placing the test element at a selected point between the first and second portions of the handle-forming material, after which the first and second handle-forming material portions are sealed or otherwise enclosed together with the test element material therebetween. The handle-forming and test element materials are then cut to form the handle element portion and test element portion of a LEAP Testing Implement.

Figure 5:
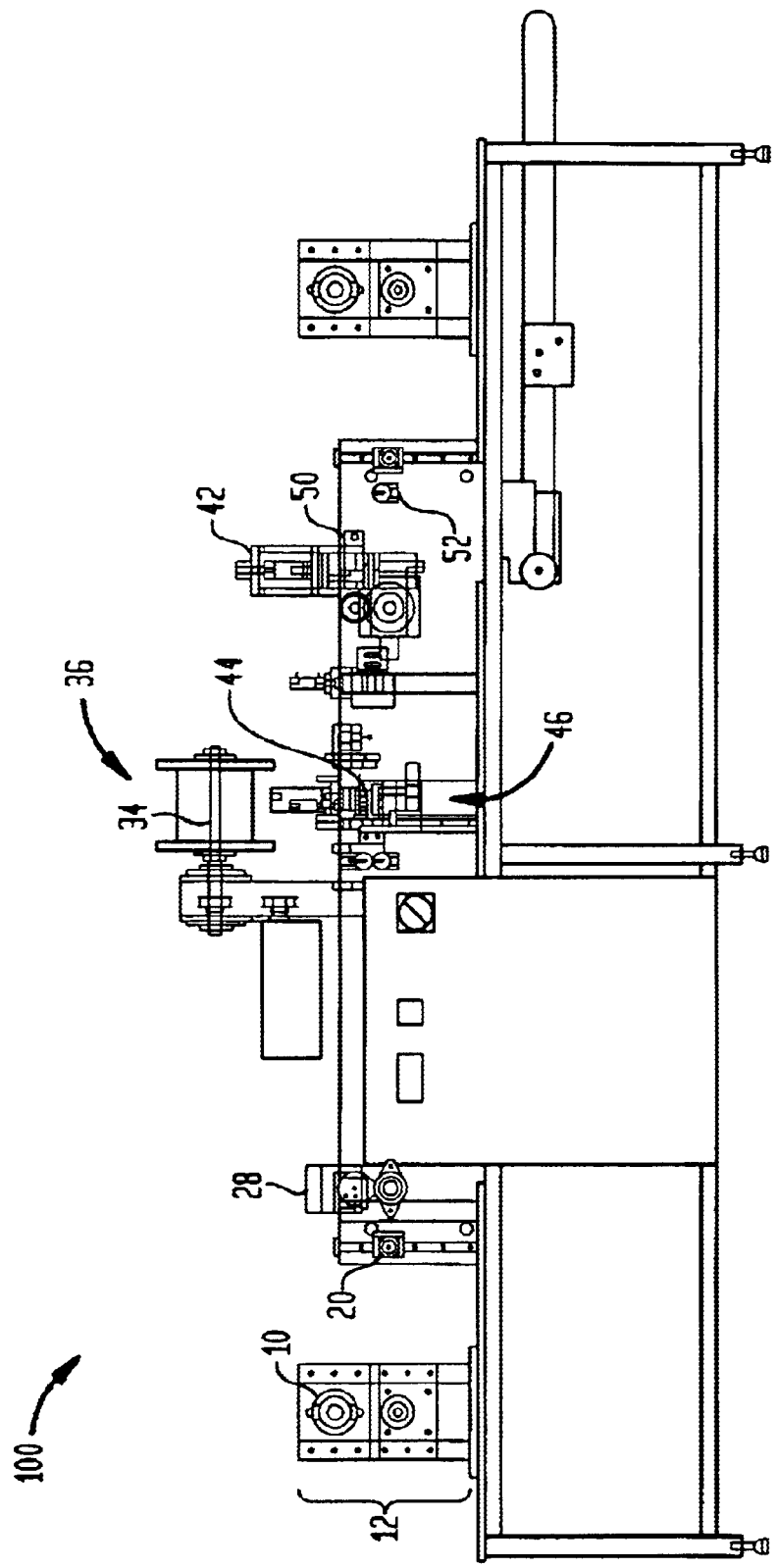
FIG. 5 is a schematic drawing of a machine for manufacturing medical test implements in accordance with the present invention.
Figure 6:
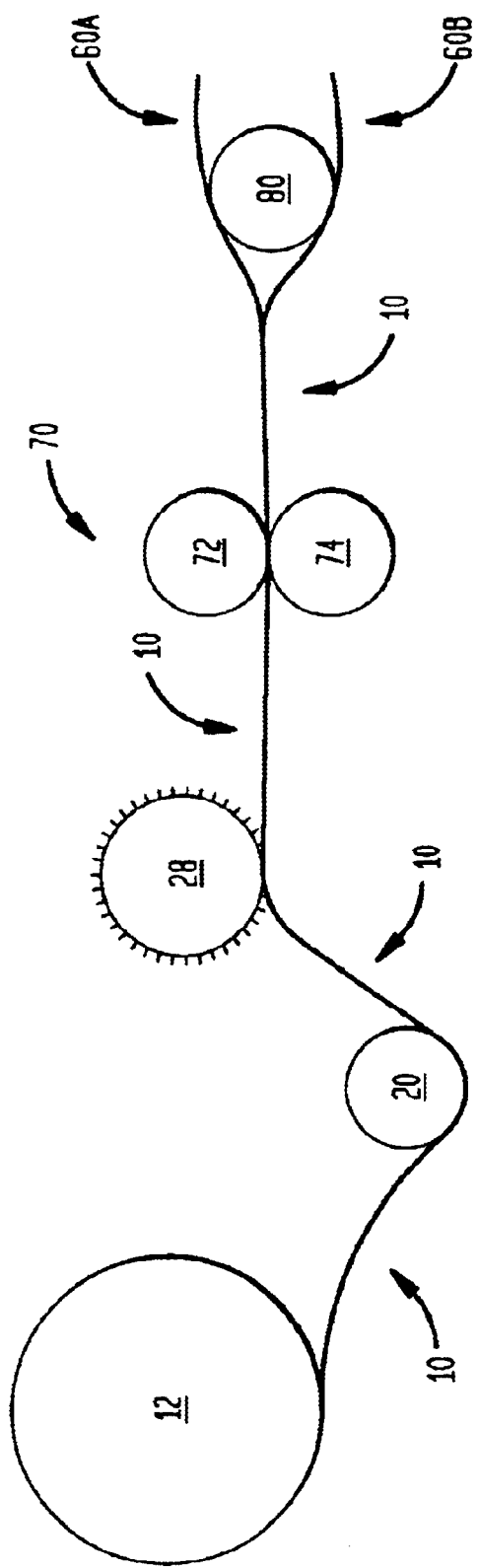
FIG. 6 is a side, schematic view of components of the machine of FIG. 5 that are used to prepare the handle-forming material prior to the insertion of filament material.
Figure 9:
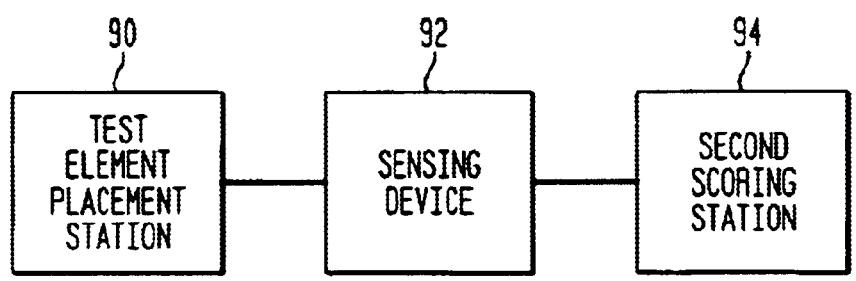
FIG. 9 is a schematic view of further components of the machine of FIG. 5.

Preferably all, or at least the majority of these steps are performed mechanically. FIG. 5 depicts an overview of the components of an exemplary medical implement manufacturing machine 100 useful to perform, and/or assist in performing, the steps of the automated process described in FIG. 4. The machine 100 produces medical implements, such as LEAP Testing Implements, with great precision and with a high throughput. Several components of the machine 100 are also shown in FIGS. 6 and 9 in schematic detail.

The production process of FIG. 4 generally commences by forming the handle portion 4 of a LEAP Testing Implement. To do so, a sheet or roll of handle-forming material 10 is mounted (e.g., by hand) on a spindle 12 of the machine 100. The machine 100 is then activated, causing the material 10 to be unwound or otherwise dispensed from the first spindle 12 as shown in FIG. 6, and to passed through several additional processing stations/components as described below.

Such stations/components may include one or more tension control bars or rollers 20, which is/are generally provided on the machine 100 to maintain appropriate tension upon the material 10 after it is unwound from the spindle 12. This roller 20 can be a so-called Adancer© roll that maintains tension upon the material 10 by moving up and down at appropriate time intervals as is generally known in the art. Optionally, the machine 100 can also include drive and idle rolls (not shown) that maintain further control of the material 10 as is generally known in the art.

Once unwound from the spindle 12, the handle-forming material 10 passes through a first scoring station, which includes a cutting wheel 28. The cutting wheel 28 is serrated or otherwise adapted for scoring/perforating the handle-forming material in order to facilitate subsequent folding thereof.

Figure 7:
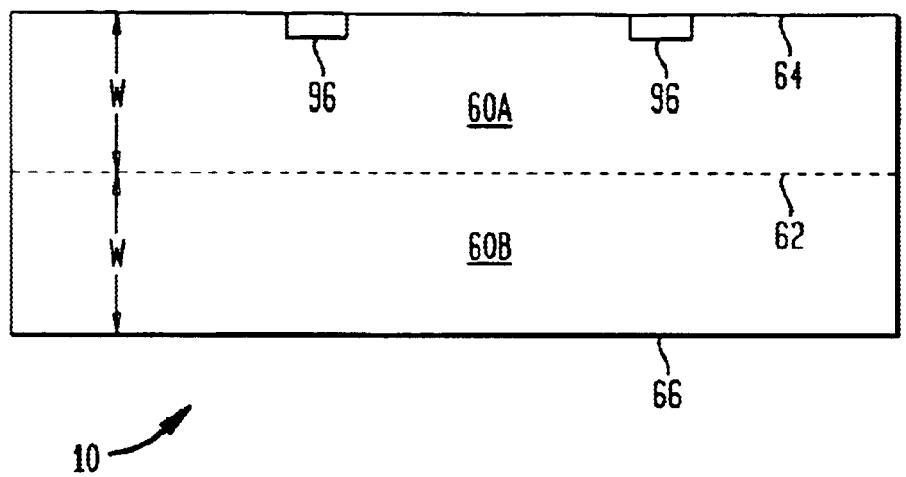
FIG. 7 is a top view of handle-forming material after being scored by the first scoring station component of the machine of FIGS. 5 and 6.

Once scored, the handle-forming material 10 is divided into at least two conjoined portions 60A 60B, wherein each portion is separated from its adjoining portion(s) by score lines 62 as shown in FIG. 7. Each portion 60A, 60B has an end 64, 66 that is located parallel to the score lines 62. The distance between these each of these ends 64, 66 and the score lines 62 represents the width W of each portion 60A, 60B of the material 10.

In an exemplary embodiment, the conjoined portions 60A, 60B of the handle-forming material 10 are identical in width W, and have identical thicknesses (not shown), although either or both the widths and thicknesses may vary. The width W is generally in the range of about 20 millimeters to 30 millimeters, preferably in the range of about 23 millimeters to 27 millimeters.

Figure 8:
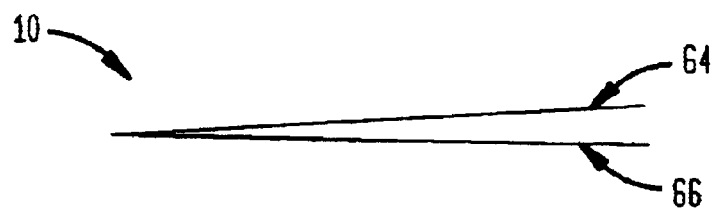
FIG. 8 is a side view of the material of FIG. 7 after its has been folded lengthwise along its score lines.

Once scored, these portions 60A, 60B are caused to be folded toward each other as they pass through a folding station 70 (see FIG. 6) of the machine. The folding station 70 generally includes two wheels 72, 74 that are positioned such that as the handle-forming material 10 is fed between the wheels, the material 10 is caused to be folded lengthwise such that the ends 64, 66 of the portions 60A, 60B of the material 10 converge toward each other as shown in FIG. 8.

Therefore, in an exemplary embodiment of the invention in which the portions 60A, 60B have equal widths W and identical thicknesses (not shown), the handle-forming material 10, following folding, has a width equal to the width W of one of the portions 60A, 60B of the material 10, and a thickness that is twice that of one of the portions 60A, 60B of the material 10.

To facilitate the folding thereof, the handle-forming material 10 should be sufficiently flexible. Exemplary flexible handle-forming materials include, but are not limited to, paper-based materials such as paperboard or cardboard, plastic materials such as polyethylene, polypropylene or nylon, or composite materials. One of ordinary skill in the art will appreciate that although it is desired that the handle-forming material 10 be sufficiently flexible, the material should be rigid enough to not deform during proper use of a LEAP Testing Implement. Moreover, it is also understood that the handle-forming material 10 may be preprinted with text, such as use instructions and/or promotional data prior to its placement on the spindle 12.

Referring again to FIG. 6, the folded handle-forming material 10, which generally has had a thermosensitive adhesive previously applied thereto as is known in the art, is then guided from the folding station 70 toward a separator device 80, which separates the first portion 60A of the handle-forming material from the second portion 60B of the handle forming material at the perforated line of the material at the existing score lines 62.

Because of the geometry of the handle-forming material 10 and the design and location of the machine's components, it is understood that the handle-forming material, once loaded onto the spindle 12, may initially be required to be guided to the separator device 80 by hand or by other suitable automated or non-automated means. In such an embodiment, the material 10 is guided from the spindle 12, under any tension control rollers 20 and then to the perforating wheel 28 of the first scoring station.

Once at the cutting wheel 28, the machine 100 is activated such that the material 10 is scored as described above, and then automatically fed through the folding station 70, also as described above. When the handle-forming material 10 emerges from the folding station 70, the machine 100 is deactivated, and the portions 60A, 60B of the material 10 are guided (e.g., by hand or other automated or non-automated means), respectively, over and under the separator device 80 and then into a test element placement station 90 (see FIG. 9). The machine 100 is then reactivated in order to continue the automated process, the next step of which is to insert and secure test element material 34 between the portions 60A, 60B of the handle-forming material 10.

The test element material 34 is provided on a roll or spool 36 that is driven by a motor (not shown) and an associated tension control device (not shown) generally as described above with respect to the handle-forming material 10. In an exemplary embodiment of the present invention, the test element material 34 is a synthetic plastic material such as nylon, but it is understood that the test element material may be any suitable plastic or non-plastic material.

As the test element material 34 is unwound or otherwise dispensed from the spool 36, it preferably passes through a heat source (not shown), in order to remove any residual roll or spool memory that could cause subsequent unwanted curvature of the test element material 34. The time during which the test element material 34 is heated in the heat source (not shown), as well as the temperature of the heat source 42 during heating are each selected based on the diameter of the test element material 34.

In an exemplary embodiment of the present invention, the test element material has a diameter in the range of about 0.4 millimeter to 0.5 millimeter. For a test element material having a diameter within this range, the heating temperature should be in the range of about 250° F. to 350° F., and the heating time should be in the range of about 20 seconds to 40 seconds.

It is understood that other factors, including, but not limited to, other dimensions of the test element material 34 and/or the type of test element material being heated may necessitate modification of the heating temperature and/or heating time outside of the above ranges in order to assuredly remove any unwanted residual roll or spool memory from the test element material.

Once the test element material 34 exits the heat source (not shown), a hitch feed 44 component of the test element placement station 90 precisely inserts it into a space defined between the first and second portions 60A, 60B of the handle-forming material such that a substantially right angle, α, (see FIG. 2) is formed between the handle-forming material 10 and the test element material 34.

In another alternate embodiment, an application component (not shown) of the placement station 90 then applies a sufficiently strong adhesive, e.g., a pull-and-stick adhesive, to the test element material 34 and/or one or both portions 60A, 60B of the handle-forming material 10. Thereafter, a heat-seal press or plate component (not shown) of the placement station 90 presses and heats the first and second portions 60A, 60B of the handle element material 10 together to securely enclose (via the activated thermosensitive adhesive already present on the handle element material) the test element material 34 between these first and second portions of the handle element material while maintaining the above-described right angle relationship.

Once sealed the handle forming material with attached test element is pulled via two drive rollers 50. These drive rollers 50 are spaced apart from each other far enough to ensure that the handle-forming material 10 (with attached test element 34) can pass between the wheels without snagging or otherwise being blocked from passage, out are close enough together to ensure advancement to the next station.

Thereafter, the handle forming material 10 (with test material 34 secured within its portions 60A, 60B) is fed into a second guillotine/perforating station 94 to produce a series of finished LEAP Testing Implements. At the guillotine/perforating station 94, the material 10 is either cut in a guillotine-like manner to form individual LEAP Testing Implements, or perforated in a horizontal matter to create conjoined LEAP Testing Implements that can be gathered, e.g., via a rewind uptake spool.

Figure 2:
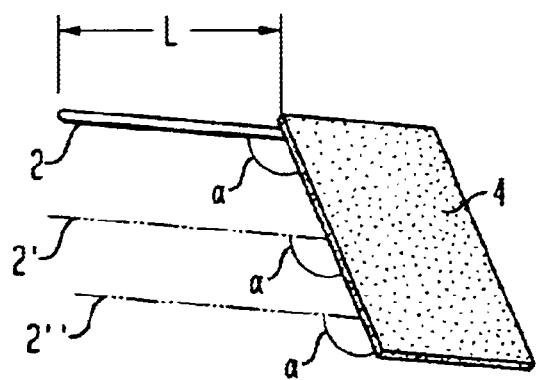
FIG. 2 is a perspective view of an exemplary LEAP Testing Implement.
Figure 3:
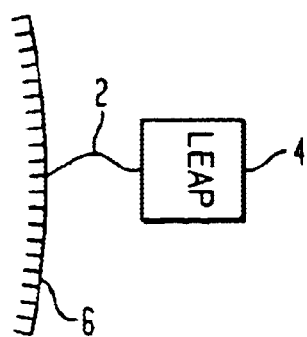
FIG. 3 illustrates the LEAP Testing Implement of FIG. 2 being applied against a plantar site.

Each finished LEAP Testing Implement has a handle element portion 4 and a test element portion 2, the test element portion extending a distance between 37 millimeters and 39 millimeters from, at an approximate right angle, α, with respect to, the handle-forming portion as shown in FIG. 2.

In an exemplary embodiment of the invention, each finished LEAP Testing Implement has a width less than its length. Generally, the width of each LEAP Testing Implement is in the range of about 20 millimeters to 30 millimeters, preferably in the range of about 23 millimeters to 27 millimeters, while the length of each LEAP Testing Implement is in the range of about 40 millimeters to 50 millimeters, preferably in the range of about 42 millimeters to 46 millimeters. It is understood, however, that each LEAP Testing Implement may have a width and/or length that falls outside of these exemplary ranges.

It is further understood that although the test element portion 2 of the LEAP Testing Implement is shown in FIG. 2 as protruding from the handle element portion 4 of the LEAP Testing Implement such that the shape of the LEAP Testing Implement resembles a flag, the test element portion 2 may protrude from the handle element portion 4 to form other Testing Implement shapes, as long as the angle of protrusion, a, is approximately a right angle and the distance of protrusion is between 37 millimeters and 39 millimeters. Exemplary, non-limiting, alternative protrusion positions of the test element portion 2 from the handle element portion 4 are shown by the dashed lines 2', 2" in FIG. 2.

Both the insertion of the test element material 34 at the test element placement station 90 and the cutting of the handle-forming material 10 by the second guillotine/perforating station 94 are controlled by the presence of an intermediary-located sensing device 92 that senses register marks 96 (see FIG. 7) that are present on the handle-forming material 10. Specifically, the sensing device 92 senses when a register mark 96 passes its viewing/sensing area and signals, as is generally known in the art, various stations/components of the machine 100 to either activate or deactivate.

In an exemplary embodiment of the present invention, when the sensing device senses a register mark 96, the spindle 12 that feeds handle-forming material 10 is signaled to stop for a predetermined time as is generally known in the art. During this predetermined time, the sensing device 92 signals the hitch feed 44 to insert test element material 34 between the portions 60A, 60B of the handle-forming material and further signals the cutting of the test element material to a predetermined length and the activation of the heat-seal press/plate portion of the test placement station 90 to seal the test element material between the portions of the handle forming material, each as is generally known in the art.

Also, during this spindle 12 stop time, the sensing device 92 concurrently signals the second guillotine/perforating station 94 to cut handle-forming material that already contains test element material. This predetermined stop time is generally in the range of about 0.5 second to 1.5 second, with approximately 1.0 second being a preferred stopping time.

Thereafter, each completed LEAP Testing Implement, including a handle element portion 4 with test element portion 2 attached thereto, is either automatically ejected into a collection container (not shown) or is otherwise retrieved for subsequent inspection and/or packaging. Optionally, the machine 100 can include a load sensor cell 52 in order to measure/verify the quality of some or all completed LEAP Testing Implement. The cell 52 is generally in the form of a membrane that presses against each completed LEAP Testing Implement to determine or forecast whether each Testing Implement will provide the proper amount of force in a patient-testing environment.

LEAP Testing Implements that provide too much or too little force are rendered markedly visually distinct from acceptable LEAP Testing Implements by guillotine cutting of the test element material, while all acceptable Leap Testing Implements are routed into the above-described collection container or are otherwise retrieved.

In an alternate embodiment of the present invention, the second guillotine/perforating station 94 does not cut through the handle-forming material 10 to form individual LEAP Test Elements. Instead, the second guillotine/perforating station 94 scores/perforates, but does not completely cut, the handle-forming material 10 to produce scoring lines that run widthwise along the still intact material 10. In an exemplary such alternate embodiment, the handle-forming material 10 (with test element material 34 attached thereto) is then routed to a take-off roll or spindle (not shown), where it is rewound either automatically or by hand. Individual finished LEAP test elements can then be removed from the rewound roll at a subsequent time either by cutting or tearing the handle-forming material 10 at the widthwise score lines.

As indicated above, one or both the portions 60A, 60B of the handle forming material 10 may be pre-treated with a thermosensitive adhesive prior to placement of the material 10 on the roll/spool 10 of the machine 100. In such an embodiment, once the test element material 34 is inserted between the portions 60A, 60B, the thermosensitive adhesive is heat activated by the heat-seal press/plate 46, thus applying a predetermined amount of heat and pressure for a predetermined time in order to securely enclose (in a right-angle relationship as discussed above) the test element material 34 between the portions 60A, 60B of the handle forming material 10.

One of ordinary skill in the art will appreciate that, in order to securely enclose the test element material 34 between the portions 60A, 60B of the handle forming material 10 in a right angle relationship, one, some or all of the amount of time, pressure and heat applied to the thermosensitive adhesive, may all vary without departing from the scope of the invention.

In yet another alternate embodiment, the test element material 34 can be enclosed securely between the first and second portions of the handle-forming material without the use of an adhesive. For example, after the test element material 34 is deposited between the first and second portions of the handle-forming material 10 by the hitch feed and the first and second portions are folded together by the seal press 46, the first portion of the handle-forming material may be stapled or otherwise mechanically connected to the first and second portions of the handle-forming material.

As noted above, it is important to ensure that the test element 2 portion of a LEAP Testing Implement has a length L (see FIG. 2) of between 37 millimeters and 39 millimeters. This can be accomplished in several manners.

In an exemplary embodiment of the invention, an over-length of test element material 34 is secured to the handle element 4 at an approximate location, after which the test element material is cut down to an appropriate length to form the test element 2. Generally, a cutting implement of the test element placement station 90 cuts or otherwise detaches test element material 34 such that a length of between 37 and 39 millimeters of the material extends from the handle element material 10.

A hitch feed mechanism 44 inserts the test element material 34 to the proper predetermined length, which is then cut. The register marks 64 (see FIG. 7) on the handle-forming material 10 activate an optical sensor device, which, in turn, regulates the exact length of the handle-forming material and, concurrently, signals the machine 100 to stop, and also to insert and then cut the test element material, which is then secured between the portions 60A, 60B of the handle forming material via the heat-seal press/plate as discussed above.

In another exemplary embodiment of the invention, a feeding mechanism (not shown) can supply prefabricated test elements 2 from a hopper or holding device (not shown). These test elements 2 will have been cut to specific lengths, and their lengths generally would have been verified as being between 37 and 39 millimeters prior to their placement in the holding device. These test elements 2 are then attached to the handle-forming material 10 in any of the manners described above, or as otherwise known in the art.

One skilled in the art will appreciate further features and advantages of the invention based on the above-described embodiments. For example, the invention may be used to produce other medical implements and/or LEAP Testing Implements with dimensions outside of the ranges discussed above. Accordingly, the invention is not to be limited by what has been particularly shown and described, except as indicated by the appended claims. All publications and references cited herein are expressly incorporated herein by reference in their entirety.

What is claimed is:

1. A method for producing a plurality of medical test implements, comprising the steps of:
   folding a continuous sheet of handle forming material at a folding station such that first and second continuous portions converge toward each other;
   guiding the first and second continuous portions, respectively, over and under a separator device;
   inserting a continuous deformable material between the first and second continuous portion of the folded sheet of handle forming material;
   joining the first and second continuous portions together with the deformable material therebetween and then cutting deformable material to form a test element;
   repeating the inserting and joining steps such that a plurality of spaced apart test elements are between the joined first and second portions of the folded sheet; and
   perforating, scoring or cutting the joined first and second portions of the folded sheet of handle-forming material to form a plurality of medical test implements, each having a handle and a test element that is adapted to deform when a predetermined load is applied thereto.

2. The method of claim 1, wherein the sheet is scored to form the sheet prior to folding the first and second portions.

3. The method of claim 1, wherein the continuous deformable material is heated to a predetermined temperature for a predetermined time before the continuous deformable material is cut to form the plurality of test elements.

4. The method of claim 3, wherein the predetermined temperature and predetermined time are selected to allow for elimination of substantially all curvature of the continuous deformable material during the elongate test element.

5. The method of claim 4, wherein the predetermined temperature is in the range of about 250° F. and 350° F.

6. The method of claim 4, wherein the predetermined time is in the range of about 20 seconds and 40 seconds.

7. The method of claim 1, wherein the length of each test element is in the range of about 37 millimeters to 39 millimeters.

8. The method of claim 1, wherein each test element has a diameter in the range of about 0.4 millimeters and 0.5 millimeters.

9. The method of claim 1, wherein the handle on each medical test implement has a width in the range of about 20 millimeters and 30 millimeters.

10. The method of claim 1, wherein the handle on each medical test implement has a length in the range of about 40 millimeters and 50 millimeters.

11. The method of claim 1, wherein the sheet is formed from a material selected from the group consisting of cardboard, paperboard, a composite material and a plastic material.

12. The method of claim 11, wherein the plastic material is selected from the group consisting of polyethylene, polypropylene, nylon, and combinations thereof.

13. The method of claim 1, wherein the test elements implements are each formed from a plastic material.

14. The method of claim 13, wherein the plastic material is nylon.

15. The method of claim 1, wherein the test element deforms when a load of approximately 10 grams is applied axially thereto.

16. The method of claim 1, further comprising the step of verifying whether the deformable test element deforms in response to the application of a predetermined load thereto.

17. The method of claim 1, further comprising the step of coating at least a portion of the sheet material with an adhesive prior to the step of joining the first and second portions to one another.

18. The method of claim 1, wherein the step of joining the first and second portions to one another comprises heating the first and second portions.

19. The method of claim 18, wherein the first and second portions are heated using a heat/seal press heated to a predetermined temperature for a predetermined time and a precise amount of pressure that facilitates sealing of the first and second portions of the material.

20. The method of claim 18, wherein the sheet has been pre-treated with a thermosensitive adhesive that is activated by the step of heating the first and second portions.

* * * * *